(12) United States Patent
Lovell et al.

(10) Patent No.: US 7,851,172 B2
(45) Date of Patent: Dec. 14, 2010

(54) BIOMARKERS OF MILD COGNITIVE IMPAIRMENT AND ALZHEIMER'S DISEASE

(75) Inventors: Mark A. Lovell, Mt. Vernon, KY (US); Bert C. Lynn, Nicholasville, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/459,763

(22) Filed: Jul. 25, 2006

(65) Prior Publication Data

US 2008/0026405 A1      Jan. 31, 2008

(51) Int. Cl.
G01N 33/53    (2006.01)
G01N 33/542   (2006.01)
G01N 33/566   (2006.01)

(52) U.S. Cl. ................ 435/7.92; 435/7.9; 435/7.1; 436/501

(58) Field of Classification Search ............... None
See application file for complete search history.

(56) References Cited

U.S. PATENT DOCUMENTS

| | | | |
|---|---|---|---|
| 4,728,605 | A | 3/1988 | Fudenberg et al. |
| 5,874,312 | A | 2/1999 | Sredni et al. |
| 6,027,896 | A | 2/2000 | Roses |
| 6,114,133 | A | 9/2000 | Seubert |
| 6,130,048 | A | 10/2000 | Nixon |
| 6,210,895 | B1 | 4/2001 | Schipper |
| 6,358,681 | B2 | 3/2002 | Ginsberg |
| 6,451,547 | B1 | 9/2002 | Jackowski |
| 6,458,549 | B2 | 10/2002 | Maesaka |
| 6,461,831 | B1 | 10/2002 | Small |
| 6,465,195 | B1 | 10/2002 | Holtzman |
| 6,475,161 | B2 | 11/2002 | Teicher |
| 6,495,335 | B2 | 12/2002 | Chojkier |
| 2001/0021508 | A1 | 9/2001 | Maesaka |
| 2004/0072261 | A1 | 4/2004 | Kostanjevecki |
| 2005/0221348 | A1 | 10/2005 | Ray et al. |
| 2005/0244890 | A1 | 11/2005 | Davies et al. |

FOREIGN PATENT DOCUMENTS

| | | |
|---|---|---|
| WO | 2006108051 | 8/2004 |
| WO | 2004001421 | 10/2006 |

OTHER PUBLICATIONS

Stark et al., 2001, J. Chromatography, 754, pp. 357-367.*
Yuan et al., 2005, Proteomics, 5, pp. 541-550.*
Castano et al., 2006, Neurolog. Research, 28, pp. 155-163.*
Zhang et al., 2005, J. Alzheimer's disease, 8, pp. 377-386.*
Biroccio et al., 2006, Proteomics, 6, pp. 2305-2313.*
Johanson et al., 2005, Blood-cerebrospinal fluid barrier, Taylor &Frances, 2005, pp. 311-343.*
Blennow, et al. Dementia. 6(6):306-11 (1995).
Burbach, et al. 2004, J. Neurosci. 24 (10), 2421-2430.
Carrette, O. et al, Proteomics, 3:1486-1494 (2003).
Davidson et al., Neuroreport, 13:611-615 (2002).
Elovaara Acta, Neurol Scand. 69(5):302-5(1994).
Fahnestock, et al., 2002, J. Neural. Transm. Suppl. 2002(62):241-52.
Harigaya et al. Intern Med. 34(6):481-4 (1995).
Harrington, et al., Appl. Theoret Electrophor 3:229-34 (1993).
Hiraoka, et al., J. Chormatogr A 802:143-48 (1998).
Hoekman, et al., Neth. J. Med. 28:551-557 (1985).
Huhmer, et al., Disease Markers 22:3-26 (2006).
Iqbal , et al., J. Neural Transm Suppl. 53:169-80 (1998).
Kawashima, Mod. Pathol. 14:197-201 (2001).
Kudo, et al., Brain Res. 639 (1): 1-7 (1994).
Li, et al., (2002, Neuroscience 113 (3): 607-15).
Mase. Neurosci Res 47:455-459 (2003).
Matsubara, et al., Ann. Neurol 28(4):561-7(1990).
McKhann, et al., Neurology 34:939-48 (1984).
Melegos, et al., Prostaglandins 54:463-474 (1997).
Merched, et al., FEBS Lett. 425(2):225-8 (1998).
Peterson, et al., Arch Neurol 56:303-308 (1999).
Price and Morris, Ann Neurol 45:358-68 (1999).
Sanna, et al., (2003, J. Clin. invest. 111(2):241-50).
Serot, et al., J Neurol Neurosurg Psychiatry. 63(4)-506-8 (1997).
Skoog, et al., Neurology. 50:966-71 (1998).
Tzuzuki, et al., Neurosci Lett, 10:171-174 (2000).
Wang, et al., Acta Neuropathol (Berl). 82(1):6-12 (1991).
Martin, et al., J. Eukaryot., Microbiol., 54(1), 2007 pp. 25-28.
Sun, et al., 2007 American Society for Mass Spectrometry, 1044-0305.

(Continued)

*Primary Examiner*—Olga N Chernyshev
(74) *Attorney, Agent, or Firm*—Viksnins Harris & Padys PLLP (57) ABSTRACT

A method for quantifying a neurodegenerative disorder in a patient that includes obtaining a fluid sample from the subject; measuring a protein biomarker complex in said fluid sample and correlating the measurement with mild cognitive impairment or Alzheimer's disease status. The biomarkers include those that comprise at least one of a transthyretin protein and/or a prostaglandin-H2 D-isomerase protein, and at least one second, different protein selected from a transthyretin, prostaglandin-H2 D-isomerase, beta-2-microglobulin, cystatin C, superoxide dismutase [Cu—Zn], plasma retinol-binding protein, phosphatidylethanolamine-binding protein, carbonic anhydrase 2, prostaglandin-H2 D-isomerase, and/or serotransferrin protein.

6 Claims, 6 Drawing Sheets

OTHER PUBLICATIONS

Wiliams, et al., Appl. Microbiol Biotechnol (2007) 74:422-432.
McCollum, et al., Experimental Neurology 2002 (2006) 506-513.
Williams, et al., Electrophoresis 2006, 27, 2984-2995.
Liu, et al, Chem. Res. Toxicol. 2006, 19, 710-718.
Wang, et al., Molecular and Cellular Biology, Dec. 2005, p. 10745-10754.
Kimball, et al., Neurobiology of Aging 27 (2006) 1239-1249.
Poon, et al., Free Radical Biology & Medicine 39 (2005) 453-462.
Kimball, et al., Brain Research 1044 (2005) 206-215.
Kimball, et al., Neuroscience 132 (2005) 313-324.
Pocernich, et al., Molecular Brain Research 133 (2005) 307-316.
Pocernich, et al., Molecular Brain Research 133 (2005) 299-306.
Kimball, et al., Journal of Neuroscience Research 79:707-713 (2005).
Poon, et al., Neurochemistry international 46 (2005) 159-168.
Poon, et al., Neuroscience 126 (2004) 915-926.
Castegna, et al., Journal of Neurochemistry, 2004, 88, 1540-1546.
Wenner, et al., Journal of Proteome Research, 2004: 3, 97-103.
Wenner, et al., Journal American Society for Mass Spectrometry, 2004, 15, 150-157.
Wiliams, et al., Neurobiology of Aging 27 (2006) 1094-1099.
Xiong, et al., Antioxidants & Redox Signaling vol. 9, No. 4, 2007.
Lovell, et al., Journal Neuropathol. Exp Neurol, vol. 64, No. 8, Aug. 2005, pp. 675-680.
Lovell, et al., Journal Neuropathol. Exp Neurol, vol. 65, No. 5, May 2006, pp. 489-498.
Wenner, et al., Journal of Proteome Research, 2004, 3, 97-103.
Mark, et al., Journal of Neurochemistry, vol. 68, No. 1, 1997.
Xie, et al., Brain Research 743 (1996) 271-277.
Sullivan, et al., The Journal of Comparative Neurology 474:524-534 (2004).
Markesberry, et al., Antioxidants & Redox Signaling, vol. 8, No. 11 & 12, 2006.
Smith, et al., NeuroToxicology 27 (2006) 1-5.
Liu, et al., Chem. Res. Toxicol. 2006, 19, 710-718.
Wang, et al., Journal of Neurochemistry. 2006, 96, 825-832.
Markesbery, et al., Annals of Neurology, vol. 58, No. 5, Nov. 2005.
Liu, et al., Anal. Chem. 2005, 77, 5982-5989.
Smith, et al., NeuroToxicoloqy 27 (2006) 1-5.
Wang, et al., Journal of Neurochemistry, 2005, 93, 953-962.
Williams, et al., Anal. Chem. 2005, 77, 3383-3389.
Lovell, et al., Neurochemical Research, vol, 30, No. 1, Jan. 2005, pp. 113-122.
Lovell, et al., Neurobiology of Aging 22 (2001) 187-194.
Lovell, et al., Arch Neurol/vol. 58, Mar. 2001.
Lovell, et al., Free Radical Biology & Medicine, vol. 29, No. 8, pp. 714-720.
Lovell, et al., Brain Research 855 (2000) 116-123.
Gabbita, et al., Journal of Neurochemistry, 73, 1660-1666 (1999).
Prasad, et al., Neurochemical Research, vol. 23, No. 1, 1998, pp. 81-88.
Lovell, et al., Neurobiology of Aging, vol. 18, No. 5, pp. 457-461 1997.
Shao, et al., Free Radical Biology & Medicine 41 (2006) 77-85.
Smith, et al., Neuroscience 140 (2006) 879-888.
Lovell, et al., Neurobiology of Aging 27 (2006) 909 -917.
Lovell, et al., Brain Research 823 (1999) 88-95.
Rulon, et al., Biological Trace Element Research, vol. 75, 2000.
Lovell, et al., Brain Research 983 (2003) 84-96.
Lovell, et al., Free Radical Biology & Medicine, vol. 28, No, 3, pp. 418-427, 2000.
Lovell, et al., Neurobiology of Aging 23 (2002) 179-186.
Lovell, et al., Journal of Alzheimer's Disease 5 (2003) 229-239.
Gabbita, et al., Journal of Neurochemistry, vol. 71, No. 5, 1998.
Xie, et al., Free Radical Biology & Medicine, vol. 25, No. 8. pp. 979-988, 1998.
Lovell, et al., Journal of Neurochemistry, vol, 72, No. 2, 1999.
Mattson, et al., Brain Research, 602 (1993) 21-31.
Lovell, et al., Journal of the Neurological Sciences 158 (1998) 47-52.
Xie, et al., Free Radical Biology & Medicine, vol. 31, No. 1, pp. 73-81, 2001.
Lovell, et al., 1594, Neurology, 45, Aug. 1995.
Hiraoka, et al., 2001, Electrophoresis, 22, pp. 3433-3437.
Stark M. et al,: Peptide repertoire of human cerebrospinal fluid: novel proteolytic fragments of neuroendocrine proteins; J. of chromatography B: Biomedical applications; 2001; vol. 754, No. 2, 2001, pp. 357-367.
Supplemental European Search Report; Sep. 14, 2009.

* cited by examiner

BIOMARKERS OF MILD COGNITIVE IMPAIRMENT AND ALZHEIMER'S DISEASE

FIELD OF THE INVENTION

The present invention relates to the field of detection and of monitoring treatment of neurodegenerative disorders, including Alzheimer's disease and mild cognitive impairment (MCI). More particularly, the present invention relates to proteinaceous biomarkers that can be measured in biological fluids, which can be used to aid in the detection of neurodegenerative disorders, including Alzheimer's disease and mild cognitive impairment.

BACKGROUND OF THE INVENTION

Alzheimer's disease (AD), an age-associated dementing disorder, currently affects 4 million Americans and is the fourth leading cause of death in the US. The prevalence of AD doubles every 5.1 years from 1% of Americans ages 65-69 to ~39% of Americans age 90-95 (Jorm et al. Acta Psychiat Scand 76:465-79 (1987). With aging of the "baby boom" generation, the largest segment of the US population, there may be 14 million Americans with AD by 2040 unless preventative strategies are developed. With a mean survival time of 8.1 years and a range of 1 to 25 years AD is a growing socio-economic and medical problem with an estimated cost of 100 billion dollars per year in the US alone.

Risk factors associated with AD include aging, presence of APOE-4 alleles, family history, head injury, low educational attainment and low linguistic ability early in life. Although mutations in presenilin 1 and 2 and the amyloid precursor protein (APP) are associated with familial AD (FAD) these cases account for less than 5% of all AD subjects. Currently, there are no known genetic mutations associated with sporadic AD.

Pathologically, the AD brain is characterized by a loss of total brain weight, neuron loss and shrinkage, synapse loss, neuropil thread formation, abundance of neurofibrillary tangles (NFT) and senile plaques (SP) and by a proliferation of reactive microglia and astrocytes in particular brain regions including the hippocampus, amygdala and nucleus basalis of Meynert (nbM).

The two hallmark pathologic markers of AD examined at autopsy are NFT and SP. NFT are intracellular deposits of hyperphosphorylated tau, a microtubule associated protein in neuronal axons. The normal function of tau is to bind tubulin in axonal microtubules and promote stabilization (Goedert et al. EMBO J 8:393-99 (1989), Buee et al. Brain Res Brain Res Rev 33:95-130 (2000)). As such, tau is essential for axonal function and transport. Tau has 30 potential phosphorylation sites (Iqbal et al. J Neural Transm Suppl 62:309-319 (2002); Buee et al. Brain Res Brain Res Rev 33:95-130 (2000) and abnormal phosphorylation is observed in AD NFT leading to a loss of ability to bind microtubules (Iqbal et al. J Neurol 59:213-222 (2000).

Senile plaques are extracellular deposits composed of a central core of amyloid β peptide (Aβ), a 40 or 42 amino acid polypeptide derived from the amyloid precursor protein (APP). Surrounding the amyloid core are dystrophic neurites and reactive glia. Formation of Aβ occurs through combined action of beta and gamma secretase cleavage of APP leading to the neurotoxic Aβ40/42. Mutations in APP associated with FAD are associated with increased generation of Aβ40/42. Mutations in presenilin-1 and 2 (gamma secretases) are also associated with FAD and lead to increased production of Aβ40/42. Although NFT and SP are the hallmark neuropathologic markers of AD, it is unclear if they are involved in the etiology of AD or are merely end products of neurodegeneration. Additionally, it has been suggested that AD pathology may begin 20 to 30 years before the onset of clinical symptoms (Davies et al. Neurology 38:1688-93 (1988); Price and Morris Ann Neurol 45:358-68 (1999)). During the preclinical period, NFT and SP increase until reaching a critical threshold when clinical symptoms appear.

Without a clear genetic influence on sporadic AD several etiologic/pathogenic hypotheses have been suggested including energy metabolism defects, deficiencies of neurotrophic factors, glutamate toxicity, mitochondrial defects, trace element toxicity and free radical mediated toxicity.

Clinically, AD is characterized by a loss of spontaneity, drive and initiative, a progressive worsening of memory, behavioral changes, onset between 40 and 90, and the absence of systemic disorders or other brain diseases. The main clinical feature of AD is a progressive cognitive decline leading to memory loss. The memory dysfunction involves impairment of learning new information which is often characterized as short-term memory loss. In the early (mild) and moderate stages of the illness, recall of remote well-learned material may appear to be preserved, but new information cannot be adequately incorporated into memory. Disorientation to time is closely related to memory disturbance.

Language impairments are also a prominent part of AD. These are often manifest first as word finding difficulty in spontaneous speech. The language of the AD patient is often vague, lacking in specifics and may have increased automatic phrases and clichés. Difficulty in naming everyday objects is often prominent. Complex deficits in visual function are present in many AD patients, as are other focal cognitive deficits such as apraxia, acalculia and left-right disorientation. Impairments of judgment and problem solving are frequently seen.

Non-cognitive or behavioral symptoms are also common in AD and may account for an even larger proportion of caregiver burden or stress than the cognitive dysfunction. Personality changes are commonly reported and range from progressive passivity to marked agitation. Patients may exhibit changes such as decreased expressions of affection. Depressive symptoms are present in up to 40% of AD subjects. A similar rate for anxiety has also been reported. Psychosis occurs in 25% of AD subjects. In some cases, personality changes may predate cognitive abnormality.

Currently, clinical diagnosis of AD is based on structured interviews (patient histories), and neuropsychological examinations coupled with imaging or neurophysiological scans (CT, MRI, PET and/or SPECT scans and EEG) to rule out other explanations of memory loss including temporary (depression or vitamin B12 deficiency) or permanent conditions (stroke) and is based on NINCDS-ADRDA Work group criteria (McKhann et al. Neurology 34:939-48 (1984) and the American Psychiatric Association Diagnostic and Statistical Manual of Mental Disorders ($4^{th}$ Ed. Washington D.C., Am Psychiatric Assoc. (1997).

Unfortunately, clinical diagnostic methods are not foolproof. Evidence based review of current literature shows clinical diagnostic accuracy of 65 to 90%. Higher accuracy rates are generally associated with specialized centers (memory disorder clinics) focused on memory disorders whereas lower rates are likely associated with primary care physicians. Additionally, accuracy of the clinical diagnosis is likely lower during early stages of the disease when symptoms are difficult to differentiate from normal age-associated cognitive decline. More recently, studies suggest that a condition termed mild cognitive impairment (MCI) represents prodromal AD and if diagnosed early represents the best opportunity for pharmaceutical intervention. The clinical criteria used for diagnosis of MCI are those of Petersen et al. (Arch Neurol 56:303-308 (1999) and include: 1) memory complaints corroborated by an informant, 2) objective memory impairment for age and education, 3) normal general cognitive function, 4) intact activities of daily living, and 5) the subject does not meet criteria for dementia.

Further complicating diagnosis and treatment of AD is the lack of a reliable biomarker that specifically identifies AD subjects, particularly early in the prodromal stage of the disease (MCI).

In view of the magnitude of the public health problem posed by AD, considerable research efforts have been undertaken to elucidate the etiology of AD as well as to identify biomarkers, characteristic proteins or metabolites objectively measured as an indicator of pathogenic processes, that can be used to diagnose and/or predict whether a person is likely to develop AD.

Most studies of biomarkers of AD have focused on measurement in the cerebrospinal fluid (CSF). CSF is produced in the choroid plexus, a leaf like structure that projects into the lateral, third and fourth ventricles of the brain (Huhmer et al. Disease Markers 22:3-26 (2006)) and is in direct contact with the extracellular space of the brain. Because of its intimate contact with the brain, pathogenic changes in the brain that result in alterations in proteins/peptides would likely be reflected in the CSF.

A number of U.S. patents and published applications relate to methods for diagnosing AD, including U.S. Pat. Nos. 4,728,605, 5,874,312, 6,027,896, 6,114,133, 6,130,048, 6,210,895, 6,358,681, 6,451,547, 6,461,831, 6,465,195, 6,475,161, 6,495,335, 2005/0244890, and 2005/0221348. Additionally, a number of reports in the scientific literature relate to certain biochemical markers and their correlation/association with AD, including Fahnestock et al., 2002, J. Neural. Transm. Suppl. 2002(62):241-52; Masliah et al., 1195, Neurobiol. Aging 16(4):549-56; Power et al., 2001, Dement. Geriatr. Cogn. Disord. 12(2):167-70; and Burbach et al., 2004, J. Neurosci. 24(10):2421-30. Additionally, Li et al. (2002, Neuroscience 113(3):607-15) and Sanna et al. (2003, J. Clin. Invest. 111(2):241-50) have investigated Leptin in relation to memory and multiple sclerosis, respectively.

Three different biomarkers in CSF have been particularly well documented: neuronal thread protein, tau (total; T-tau and various phosphorylated forms; P-tau) and derivatives of amyloid precursor protein (APP) including $A\beta_{40}$ and $A\beta_{42}$.

Neuronal thread protein is described to be overexpressed in brain neurons in AD patients. A quantitative test for measuring levels of a specific type of neuronal thread protein (AD7c-NTP) in CSF and urine has been developed. Quite a number of studies have evaluated CSF-tau as an ante-mortem marker for AD mainly using enzyme-linked immunoabsorbent assays (ELISA) as the measurement assay. In past studies, total tau (T-tau) has been measured although there is an increasing body of literature also describing the analysis of phosphorylated (P-tau) variants of the same protein involved in the formation of NFTs. ELISAs that can distinguish between the major form of Aβ ending at amino acid 40 ($A\beta_{40}$) and the senile plaque forming species ending at position 42 ($A\beta_{42}$) have also been developed and evaluated extensively for CSF analysis. These three assays, either used individually, or in the case of tau and Aβ 42, in combination, have not demonstrated the required sensitivity and specificity values for routine clinical use, particularly for early diagnosis and discrimination between AD and other non-AD dementias. In addition, attempts to measure tau and $A\beta_{42}$ in blood have been met with limited success, further restricting their widespread adoption into clinical practice.

A wide spectrum of other aberrations, other than NTP, Tau and Aβ, has been reported in AD patient CSF. Many of the identified (protein sequence confirmed) CSF markers reported herein have been shown to be either increased or decreased in AD patients versus normal individuals. For example, the protein Ubiquitin is known to complex with hyperphosphorylated Tau during maturation of NFTs in the brains of AD patients (Iqbal et. al. J Neural Transm Suppl. 53:169-80 (1998)). Ubiquitin levels in CSF of AD and neurological control groups have been shown to be significantly higher than those of non-neurological aged controls (Wang et. al. Acta Neuropathol (Berl). 82(1):6-12 (1991); Kudo et. al. Brain Res. 639(1):1-7 (1994)).

The acute phase/inflammatory protein alpha(1)-antichymotrypsin (ACT) is overproduced in the AD brain. ACT also can promote the formation of, and is associated with, neurotoxic amyloid deposits (Potter et. al. Neurobiol Aging. 22(6): 923-30 (2001)). The levels of ACT in both serum and CSF are significantly and specifically higher in patients with Alzheimer-type dementia than in control subjects (Matsubara et. al. Ann Neurol. 28(4):561-7(1990)). There is a particularly close association of increases in CSF-ACT with late onset AD (Harigaya et. al. Intern Med. 34(6):481-4 (1995)).

Chromogranin A (CrA) is the major protein of large dense-core synaptic vesicles and may be of value as a biochemical marker for synaptic function in AD. One report described no difference between AD, vascular dementia, and age-matched control groups except when comparing a familial subtype (AD Type I) with controls where there was a statistically significant elevation of CSF CrA in the diseased individuals (Blennow et. al. Dementia. 6(6):306-11 (1995)).

Beta-2-Microglobulin (β2M) is an initiator of inflammatory responses modulated by interferons and certain cytokines (Hoekman et.al. Neth. J. Med. 28:551-557 (1985)). A proteome analysis of CSF by two-dimensional electrophoresis (2D-gel) has shown a significant increase of β2M in AD patients (Davidsson et al., Neuroreport, 13:611-615 (2002)), and more recently these results were confirmed by SELDI analysis (Carrette, O. et. al., Proteomics, 3:1486-1494 (2003)).

Transthyretin (TTR) has been shown to interact with Aβ, possibly preventing amyloid formation in biological fluids and in the brain. (Tsuzuki et al., Neurosci Lett, 10:171-174 (2000)). One identified TTR isoform was shown to be increased in AD-CSF using 2D gel analysis of a small number of AD and control patients (Davidsson, supra.). However, this result conflicts with other reports showing a clear decrease of TTR in CSF from AD patients compared with controls (Serot et. al. J Neurol Neurosurg Psychiatry. 63(4):506-8 (1997); Riisoen et. al. Acta Neurol Scand. 78(6):455-9 (1998)). This decrease is also negatively correlated with the senile plaque (SP) abundance (Merched et. al. FEBS Lett. 425(2):225-8 (1998)).

Cystatin C, a cysteine protease inhibitor, has been implicated in the neurodegenerative and repair processes of the nervous system, and the deposition of the same protein together with beta amyloid peptide was found as cerebral amyloid angiopathy (CAA) in different types of dementias (Levy et.al. J. Neuropathol. Exp. Neurol. 60:94-104). Full length Cystatin C was found as a CSF marker for AD in a previous SELDI profiling study (Carrette, supra.). A relative blood-brain barrier (BBB) dysfunction is associated with AD among very elderly individuals. The CSF/serum albumin ratio can be used as a measure of BBB function. Mean CSF/serum albumin ratio has been reported to be higher in all dementias studied, including AD, than in nondemented individuals (Skoog et al, Neurology. 50:966-71 (1998)).

Transferrin (TF) plays a role in anti-oxidant defense in serum and is also produced in the brain where its role in oxidative stress is unclear. A study on Down's syndrome patients suffering from progressive dementia showed decreased levels of TF when compared to age-matched controls with no neurological disease (Elovaara Acta Neurol Scand. 69(5):302-5(1994)).

Prostaglandin-D-Synthase (PDS) functions to convert prostaglandin H2 to prostaglandin D2 and has been identified in several studies of CSF (Harrington et al. Appl Theoret Electrophor 3:229-34 (1993); Hiraoka et al. J Chormatogr A 802:143-48 (1998); Kiraoka et al. Electorphorsis 22:3433-3437 (2001); Kawashima Mod. Pathol 14:197-201 (2001); Mase et al. Neurosci Lett 270:188-190; Mase Neurosci Res 47:455-459 (2003); Melegos et al. Prostaglandins 54:463-474 (1997)). Additionally, PDS demonstrates altered isoforms in neurologic disorders including AD and Parkinson's disease.

The present inventors have addressed the above-identified needs by identifying a protein-protein complex that is present in AD and MCI CSF and not age-matched control subjects. Additionally, the present inventors have invented a diagnostic test based on the detection of the protein-protein complex that identifies AD and MCI subjects with a high degree of specificity. Levels of these protein-protein complexes can serve as biomarkers to preferentially identify subjects with AD from age-matched control subjects or subjects with other neurologic disorders. In addition, these biomarker complexes can be used to identify subjects with mild cognitive impairment (MCI), the earliest clinical manifestation of AD.

The diagnostic test of the present invention is of considerable interest and benefit because of its ability to identify subjects with AD, particularly early in the progression of the disease (MCI). The tests of the present invention may also be used to monitor efficacy of treatment.

SUMMARY OF THE INVENTION

As indicated herein, an embodiment of the present invention provides a method for the diagnosis of MCI and AD or methods of aiding in the diagnosis of neurological disorders, including AD, by quantifying the amount of a protein-protein complex-based biomarker in a biological fluid sample of the subject, such as a cerebrospinal fluid, and comparing the measured amount with a reference value for the biomarker. The information thus obtained may be used to aid in the diagnosis, or to diagnose the disease in the individual. The protein complex-based biomarkers are differentially present in subjects having a neurological disease, including AD, versus subjects free of the disease, or subjects having a different form of dementia.

One embodiment of the present invention is a method of diagnosing or assessing the likelihood that a patient is afflicted with a neurological disease, including AD, the method comprising measuring a level of a protein complex biomarker of the present invention.

Another embodiment of the present invention is a method comprising monitoring the progression of a neurodegenerative disease, including AD, comprising measuring a level of a protein complex biomarker of the present invention.

Another embodiment of the present invention comprises monitoring the efficacy of a treatment method of a neurodegenerative disease, including AD, comprising measuring a level of a protein complex biomarker of the present invention.

Another embodiment of the present invention comprises qualifying a neurodegenerative disease, including AD, in a subject, comprising measuring a level of a protein complex biomarker of the present invention.

In the above and other embodiments of the present invention, the measured level of the biomarker is correlated with neurological disease. In embodiments, this may be accomplished by comparing the measured amount to a reference value for the biomarker. The reference value can be obtained by measuring an amount of the biomarker in age-matched control subjects that are not affected by the disease, or that are free of the disease.

Another embodiment of the present invention comprises monitoring the efficacy of a treatment method of a neurodegenerative disease, including AD, comprising measuring a level of a protein complex biomarker of the present invention. In embodiments, the efficacy of treatment is measured by monitoring levels of the biomarker in the subject compared to a reference, and/or compared to other previous tests of the subject.

In embodiments of the present invention, the biomarker of the present invention includes a complex comprised of a transthyretin molecule and a prostaglandin-H2 D-isomerase molecule.

Accordingly, one aspect of the present invention is a method of aiding diagnosis, or diagnosing a neurological disorder, comprising comparing a measured level of a biomarker that comprises transthyretin and prostaglandin-H2 D-isomerase in a biological fluid sample from an individual to a reference level for the biomarker.

In other aspects, the above method further comprises the step of managing the individual treatment based on the status. For example, if measurement of the biomarker correlates with the presence of Alzheimer's disease, then managing treatment comprises administering a drug to slow the progression of the disease. Further measurements can be compared to the previous measurements, or the standard to monitor the progression of the disease.

In a further aspect of the invention, the method further comprises measuring the biomarker after treatment has begun, to monitor the progression of the disease.

In still another aspect, the present invention provides a kit comprising a solid support comprising at least one capture reagent attached thereto, wherein the capture agent binds one component of the biomarker protein complex of the present invention. The kit also contains a second reagent to interact with the second portion of the trapped complex and reagents to measure levels of the second protein.

Other features, objects, and advantages of the invention and its various embodiments will become apparent from the instant disclosure, including the detailed description, examples, and claims.

DESCRIPTION OF THE INVENTION

In embodiments of the present invention, the protein complexes of the preset invention are markers for neurodegenerative diseases, including mild cognitive impairment and Alzheimer's disease. Levels of the protein complex of the present invention are elevated in bodily fluids, including cerebrospinal fluid, as compared to normal, non-demented age and gender-matched controls and comparatively demented patients. Thus, the biomarkers of the present invention can be used to classify a subject sample as having MCI, Alzheimer's, or normal.

DEFINITIONS

As used herein, the terms "Alzheimer's patient", "AD patient", and "individual diagnosed with AD" all refer to an individual who has been diagnosed with AD or has been given a probable diagnosis of Alzheimer's Disease (AD).

When used herein, methods for "aiding diagnosis" refer to methods that assist in making a clinical determination regarding the presence, or nature, of the AD or MCI, and may or may not be conclusive with respect to the definitive diagnosis. Accordingly, for example, a method of aiding diagnosis of AD can comprise measuring the amount of one or more AD biomarkers in a biological sample from an individual.

When used herein, the term "predicting" refers to making a finding that an individual has a significantly enhanced probability of developing a certain neurological disease.

As used herein, the phrase "neurological disease" refers to a disease or disorder of the central nervous system. Neurological diseases include multiple sclerosis, neuropathies, and neurodegenerative disorders such as AD, Parkinson's disease, amyotrophic lateral sclerosis (ALS), mild cognitive impairment (MCI) and frontotemporal dementia.

As used herein, "biological fluid sample" encompasses a variety of fluid sample types obtained from an individual and can be used in a diagnostic or monitoring assay. The definition encompasses whole blood, blood serum or blood plasma, cerebrospinal fluid (CSF), urine and other liquid samples of biological origin. The definition also includes samples that have been manipulated in any way after their procurement, such as by treatment with reagents, solubilization, or enrichment for certain components, such as proteins or polynucleotides.

An "individual" is a mammal, more preferably a human. Mammals include, but are not limited to, humans, primates, farm animals, sport animals, rodents and pets.

A "Normal" individual or sample from a "Normal" individual as used herein for quantitative and qualitative data refers to an individual who has or would be assessed by a physician as not having AD or MCI, and has an Mini-Mental State Examination (MMSE) (referenced in Folstein et al., J. Psychiatr. Res 1975; 12:1289-198) score or would achieve a MMSE score in the range of 25-30. A "Normal" individual is generally age-matched within a range of 5 to 10 years, including but not limited to an individual that is age-matched, with the individual to be assessed.

An individual with "mild cognitive impairment" is an individual who meets the following clinical criteria of amnestic MCI (Petersen et al. Arch Neurol 56:303-308 (1999): 1) memory complaints corroborated by an informant, 2) objective memory impairment for age and education, 3) normal general cognitive function, 4) intact activities of daily living, and 5) the subject does not meet criteria for dementia.

An "individual with moderate (early) AD (EAD)" is an individual who demonstrate the following criteria: 1) a decline in cognitive function for a previous higher level, 2) declines in one or more areas of cognition in addition to memory, 3) a clinical dementia rating scale score of 0.5 to 1, and 4) a clinical examination that excluded other causes of dementia.

An "individual with severe (late stage) AD (LAD)" is an individual who meets the standard clinical diagnostic criteria for probable AD (McKhann et al. Neurology 34:939-48 (1984).

As used herein, the term "treatment" refers to the alleviation, amelioration, and/or stabilization of symptoms, as well as delay in progression of symptoms of a particular disorder. For example, "treatment" of AD includes any one or more of: elimination of one or more symptoms of AD, reduction of one or more symptoms of AD, stabilization of the symptoms of AD (e.g., failure to progress to more advanced stages of AD), and delay in progression (i.e., worsening) of one or more symptoms of AD.

As used herein, a "reference value" can be an absolute value; a relative value; a value that has an upper and/or lower limit; a range of values; an average value; a median value, a mean value, or a value as compared to a particular control or baseline value. A reference value can be based on an individual sample value, such as for example, a value obtained from a sample from the individual with AD, MCI or cognitive impairment, but at an earlier point in time, or a value obtained from a sample from an AD patient other than the individual being tested, or a "normal" individual, that is an individual not diagnosed with AD. The reference value can be based on a large number of samples, such as from AD patients or normal individuals or based on a pool of samples including or excluding the sample to be tested.

As used herein, "a", "an", and "the" can mean singular or plural (i.e., can mean one or more) unless indicated otherwise.

As indicated herein, the present invention involves biomarkers. A biomarker is a characteristic biomolecule which is differentially present in a sample taken from a subject of one phenotypic status (e.g., having a disease) as compared with another phenotypic status (e.g., not having the disease). A biomarker is differentially present between different phenotypic statuses if the mean or median expression level of the biomarker in the different groups is calculated to be statistically significant. Biomarkers, alone or in combination, provide measures of relative risk that a subject belongs to one phenotypic status or another. Therefore, they are useful as markers for disease (diagnostics), therapeutic effectiveness of a drug (theranostics) and drug toxicity.

In this invention, novel biomarkers are discussed that are differentially present in subjects having neurodegenerative diseases such as AD versus subjects free of the disease. In addition, the present invention provides methods of using the protein complex-based biomarkers to qualify Alzheimer's disease in a subject.

The biomarker complex was discovered using molecular weight fractionation to isolate proteins between about 50 and 100 kDa, 2-dimensional electrophoresis and MALDI mass spectrometry for protein identification. Protein identification was based on database searches using SEQUEST™. Based on initial studies of proteins isolated between 50 and 100 kDa, several proteins of molecular weight less than 50 kDa were identified. Using 1-dimenstional electrophoresis and Western blot analysis, a band of ~55 kDa was identified that was immunopositive for both prostaglandin-d-synthase and transthyretin suggesting a protein complex or aggregate. Based on these observations, an embodiment of the present invention, an enzyme linked immunoassay (ELISA) was developed that traps prostaglandin-D-synthase and probes for and quantifies attached transthyretin.

More specifically, to interrogate CSF for novel biomarker proteins, the present inventors subjected ventricular CSF obtained at autopsy from late stage AD (LAD) and age-matched control subjects to molecular weight (MW) fractionation and 2-dimensional electrophoresis. Mass spectrometry of these molecular weight fractions showed the presence of a series of proteins in MW fractions higher than expected which among other scenarios, suggested that these proteins may be part of an aggregate or complex.

Using this approach, the present inventors identified differentially expressed proteins in LAD CSF, including beta-2-microglobulin, carbonic anhydrase, cystatin C, copper/zinc superoxide dismutase (Cu/Zn SOD), phosphytidylethanolamine binding protein, plasma retinol binding protein, prostaglandin-d-synthase (PDS), serotransferrin and transthyretin (TTR). Under normal conditions, most of the observed differentially expressed proteins except serotransferrin and homotetrameric TTR would be expected to be in the less than about 50 kDa fraction. Western blot analysis of fractionated CSF samples showed a band of ~55 kDa that was immunopositive for Cu/Zn SOD, TTR and PDS. In addition to the higher molecular weight band, bands corresponding to the native monomeric proteins were also observed using each antibody suggesting loss of native protein from the complex following addition of denaturing gel loading buffer.

Comparison of levels of native monomeric proteins showed no significant differences between LAD and control subjects for PDS or Cu/Zn SOD. Levels of monomeric TTR (MW ~16 kDa) showed a significant elevation in LAD CSF although there was considerable overlap of individual subject values between the two populations, limiting the usefulness of the native proteins as a diagnostic biomarker. In contrast, levels of the ~55 kDa band immunopositive for PDS and TTR showed significant differences between LAD and control subjects with minimal overlap between the 2 populations. Calculation of the product of staining intensity using anti-TTR and anti-PDS showed about a 10 fold increase in LAD compared to age-matched controls with virtually no overlap between the populations. Additionally, analysis of ventricular CSF specimens from MCI, early AD (EAD) and LAD subjects showed the complex was significantly elevated in MCI subjects and that levels increased in a disease-progression related manner.

To determine if the protein-protein complex is present in lumbar CSF, a small number of samples from living, probable AD and age-matched control subjects was analyzed and showed similar trends with significant elevations in probable AD CSF compared to controls. Based on identification of components of the protein complex, a sandwich enzyme linked immunoassay (ELISA) is utilized that traps a first component of the complex and probes for a second component. For example, in embodiments of the present invention, the sandwich ELISA traps a PDS and probes for the second component, TTR.

Preliminary analysis of a small number of ventricular CSF specimens from MCI, EAD, LAD and age-matched control subjects showed the complex was significantly elevated in MCI (122±24 ng/ml), EAD (120±17 ng/ml) and LAD (115±20 ng/ml) subjects compared to age-matched controls (<5 ng/ml). Additionally, CSF from subjects with other neurologic disorders including Parkinson's disease (PD), diffuse Lewy body disease (DLB), progressive supranuclear palsy (PSP) and frontotemporal dementia (FTD) showed concentrations <5 ng/ml, suggesting a high degree of sensitivity/specificity for the diagnosis of AD. Preliminary analysis of lumbar CSF specimens from a small number of living, probable AD and age-matched controls showed that the protein complex is present in probable AD subjects (about 37.5±6.2 ng/ml) and that it is about 100% sensitive and about 93% specific in the identification of AD subjects compared to age-matched controls (about <5 ng/ml) with minimal overlap between the subject populations.

Such data suggest that levels of a unique protein complex consisting of embodiments of the present invention, including TTR and PDS, may serve as a sensitive and specific diagnostic biomarker of AD and more importantly appears to identify subjects with MCI.

Reference Levels

The reference level used for comparison with the measured level for a AD biomarker may vary, depending on aspect of the invention being practiced, as will be understood by one of ordinary skill in the art. For AD diagnosis methods, the "reference level" is typically a predetermined reference level, such as an average of levels obtained from a population that is not afflicted with AD or MCI, but in some instances, the reference level can be a mean or median level from a group of individuals including AD patients. In some instances, the predetermined reference level is derived from (e.g., is the mean or median of) levels obtained from an age-matched population.

For MCI diagnosis methods (i.e., methods of diagnosing or aiding in the diagnosis of MCI), the reference level is typically a predetermined reference level, such as an average of levels obtained from a population that is not afflicted with AD or MCI, but in some instances, the reference level can be a mean or median level from a group of individuals including MCI and/or AD patients. In some instances, the predetermined reference level is derived from (e.g., is the mean or median of) levels obtained from an age-matched population.

For AD monitoring methods (e.g., methods of diagnosing or aiding in the diagnosis of AD progression in an AD patient), the reference level may be a predetermined level, such as an average of levels obtained from a population that is not afflicted with AD or MCI, a population that has been diagnosed with MCI or AD, and, in some instances, the reference level can be a mean or median level from a group of individuals including MCI and/or AD patients. Alternately, the reference level may be a historical reference level for the particular patient (e.g., a level that was obtained from a sample derived from the same individual, but at an earlier point in time). In some instances, the predetermined reference level is derived from (e.g., is the mean or median of) levels obtained from an age-matched population.

For AD stratification methods (i.e., methods of stratifying AD patients into mild, moderate and severe stages of AD), the reference level is normally a predetermined reference level that is the mean or median of levels from a population which has been diagnosed with AD or MCI (preferably a population diagnosed with AD) In some instances, the predetermined reference level is derived from (e.g., is the mean or median of) levels obtained from an age-matched population.

Age-matched populations (from which reference values may be obtained) are ideally the same age as the individual being tested, but approximately age-matched populations are also acceptable. Approximately age-matched populations may be within 1, 2, 3, 4, or 5 years of the age of the individual tested, or may be groups of different ages which encompass the age of the individual being tested. Approximately age-matched populations may be in 2, 3, 4, 5, 6, 7, 8, 9, or 10 year increments (e.g. a "5 year increment" group which serves as the source for reference values for a 62 year old individual might include 58-62 year old individuals, 59-63 year old individuals, 60-64 year old individuals, 61-65 year old individuals, or 62-66 year old individuals).

Comparing Levels of AD Biomarkers

The process of comparing a measured value and a reference value can be carried out in any convenient manner appropriate to the type of measured value and reference value for the AD biomarker at issue. For example, 'measuring' can be performed using quantitative or qualitative measurement techniques, and the mode of comparing a measured value and a reference value can vary depending on the measurement technology employed. The example, the measured values used in the methods of the invention will most commonly be quantitative values (e.g., quantitative measurements of concentration, such as nanograms of AD biomarker per milliliter of sample, or absolute amount). As with qualitative measurements, the comparison can be made by inspecting the numerical data, by inspecting representations of the data (e.g., inspecting graphical representations such as bar or line graphs).

As an example, a measured value is generally considered to be substantially equal to or greater than a reference value if it is at least about 95% of the value of the reference value (e.g., a measured value of 1.71 can be considered substantially equal to a reference value of 1.80). A measured value is considered less than a reference value if the measured value is less than 95% of the reference value (e.g., a measured value of 1.7 can be considered less than a reference value of 1.80).

One embodiment of the present invention is a method for quantifying a neurodegenerative disorder in a patient that comprises obtaining a fluid sample from the subject, and measuring a protein biomarker complex in said fluid sample. In embodiments of the present invention, the biomarker comprises at least one of transthyretin and/or prostaglandin-H2 D-isomerase, and at least one second protein selected from transthyretin, prostaglandin-H2 D-isomerase, beta-2-microglobulin, cystatin C, superoxide dismutase [Cu—Zn], plasma retinol-binding protein, phosphatidylethanolamine-binding protein, carbonic anhydrase 2, prostaglandin-H2 D-isomerase, and/or serotransferrin. Mild cognitive impairment or Alzheimer's disease status is determined by correlating the obtained measurement with standards.

In a preferred embodiment of the present invention, the protein biomarker complex comprises transthyretin and prostaglandin-H2 D-isomerase.

In another embodiment of the present invention, the measuring step comprises trapping by enzyme linked immunosorbent assay (ELISA) at least one of transthyretin and/or prostaglandin-H2 D-isomerase; and probing for a second, different protein selected from the group consisting of at least one of transthyretin, prostaglandin-H2 D-isomerase, beta-2-microglobulin, cystatin C, superoxide dismutase [Cu—Zn], plasma retinol-binding protein, phosphatidylethanolamine-binding protein, carbonic anhydrase 2, prostaglandin-H2 D-isomerase, and/or serotransferrin is identified by probing the trapped protein.

In the correlating step, the amount of said protein biomarker complex with a reference value in a control sample can be compared. In embodiments, the control sample is from a normal individual. The control sample can be compared with a previous sample taken from a patient. Additionally, the method can comprise comparing the control sample with the fluid sample of the subject to determine the progression of the mild cognitive impairment or the Alzheimer's disease.

Preferably, the sample is cerebrospinal fluid, which can be collected via a spinal tap.

In one aspect of the present invention, the process may be used as a method of monitoring the progression of a neurological disorder. In this aspect, a first measured level of a biomarker complex of the present invention is compared with a reference level of the biomarker complex, and after allowing a period of time to pass, comparing a second measured level of the biomarker complex to said reference level and/or to said first measured level of the biomarker complex. Following this comparison, the progression of the disease based on the first and second measured level of said biomarker complex can be determined.

Another aspect of the present invention is a diagnostic kit for quantifying Alzheimer's disease status. The kit may comprise a solid support coated with an antibody to capture at lease one of a protein complex selected from prostaglandin-D-synthase and/or transthyretin; and a second primary antibody to recognize the second component of the protein complex, the second component selected from a transthyretin, prostaglandin-H2 D-isomerase, beta-2-microglobulin, cystatin C, superoxide dismutase [Cu—Zn], plasma retinol-binding protein, phosphatidylethanolamine-binding protein, carbonic anhydrase 2, prostaglandin-H2 D-isomerase, and/or serotransferrin protein.

In embodiments, the solid support is a 96 well polystyrene microtiter plate. In others, the solid support is coated with anti-prostaglandin-D-synthase for protein capture.

In embodiments, the second primary antibody recognizes the second component of the protein complex (i.e., rabbit anti-human transthyretin), and a horseradish peroxidase conjugated secondary antibody against the species used to generate the second primary antibody (ie goat anti-rabbit), TMB color reagent and stopping solutions.

Figure 1:
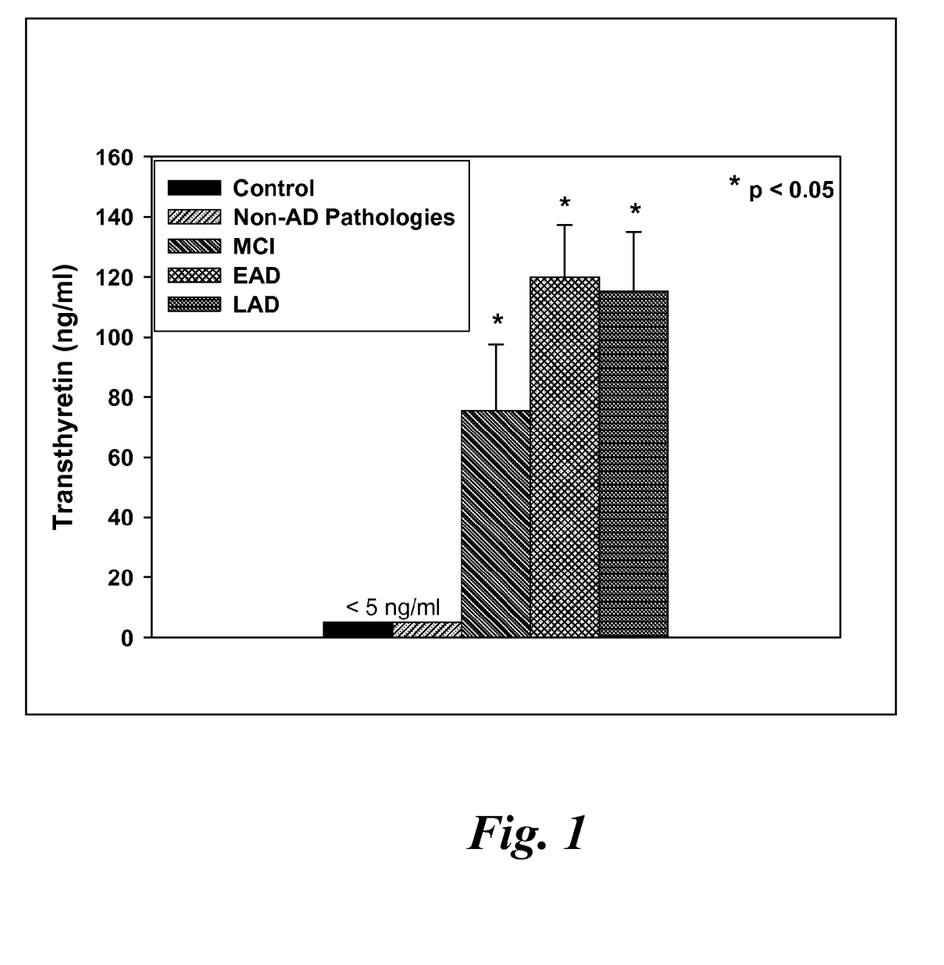
FIG. 1 is a graph showing levels of the protein complex biomarker measured as ng/ml complexed transthyretin in ventricular CSF from subjects with non-AD neuropathologies, MCI, EAD, LAD and age-matched control subjects.

With respect to embodiments of the present invention, FIG. 1 shows an embodiment of the present invention where analysis of ventricular CSF from autopsy-confirmed MCI (N=5), EAD (N=4), late stage AD (N=9) and age-matched control subjects (N=8) shows that presence of the protein complex measured as ng/ml Transthyretin identifies MCI and AD subjects with a high degree of specificity (100%) and sensitivity (AD; 100%; MCI 80%).

Figure 2:
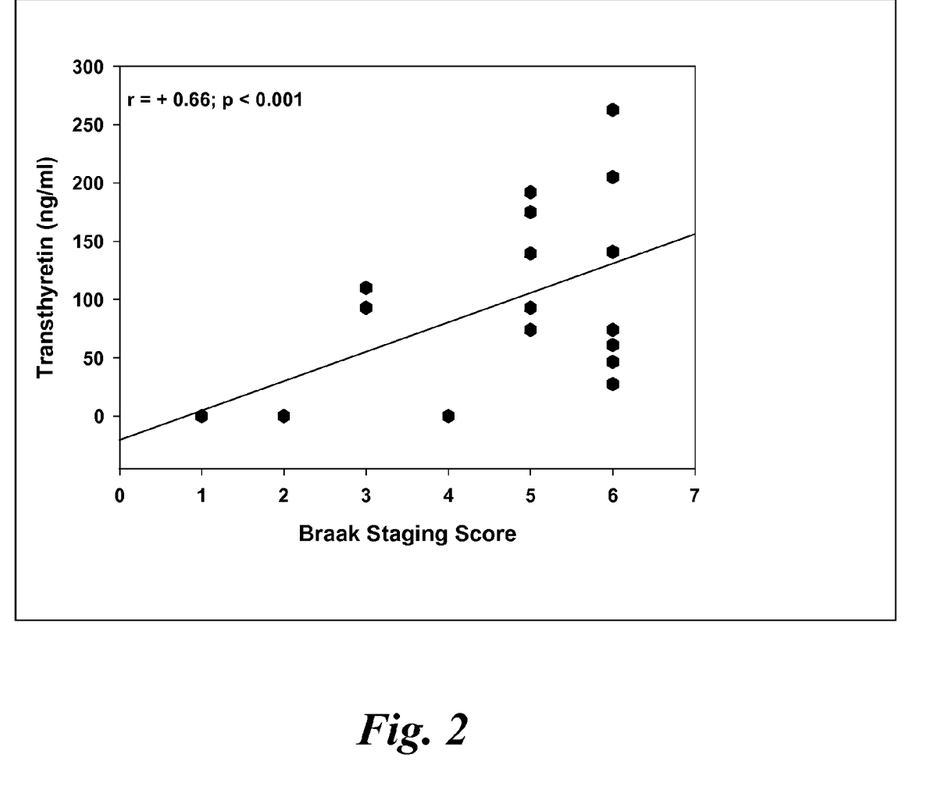
FIG. 2 is a graph showing a statistically significant positive correlation exists between levels of complexed transthyretin as a measure of the protein complex and Braak staging scores, a measure of NFT pathology (higher Braak score—more severe pathology).

FIG. 2 shows a statistically significant positive correlation between levels of the protein complex and Braak staging scores, a measure of NFT pathology. Analysis of ventricular CSF from non-AD pathologies including diffuse Lewy body disease (N=5), Parkinson's disease (N=2), parasupranuclear palsy (N=2) and frontotemporal dementia (N=2) shows 100% specificity of the biomarker complex for AD and MCI.

Figure 3:
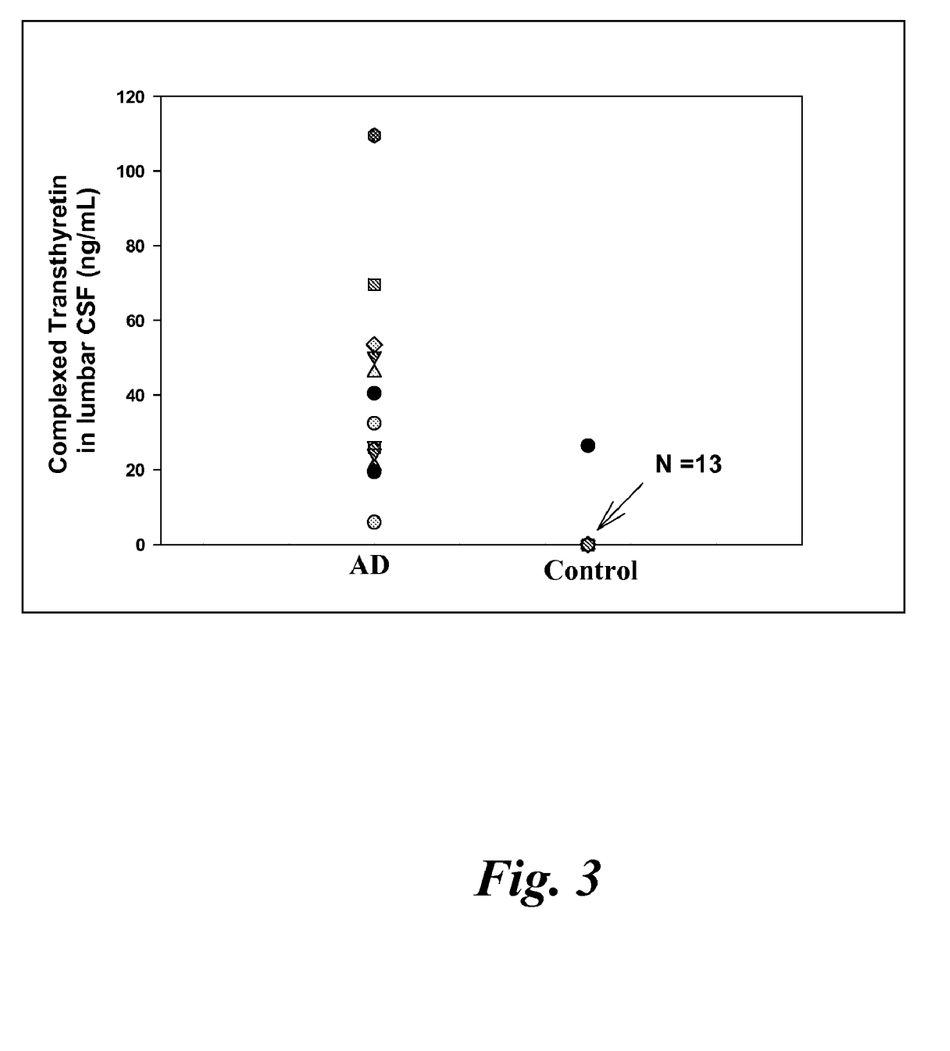
FIG. 3 is a graph showing individual concentrations of the protein complex biomarker measured as ng/ml complexed transthyretin in CSF samples from living probable AD and age-matched control subjects. All control subjects (N=13) except for 1 showed levels of the protein complex below the minimum detection limit (mean±SEM=3.6±0.7 ng/ml).

Doubly blinded analysis of lumbar CSF from living AD (N=15) and age-matched control subject (N=14) shows 100% sensitivity and 93% specificity in identification of AD and control subjects (FIG. 3).

Figure 4:
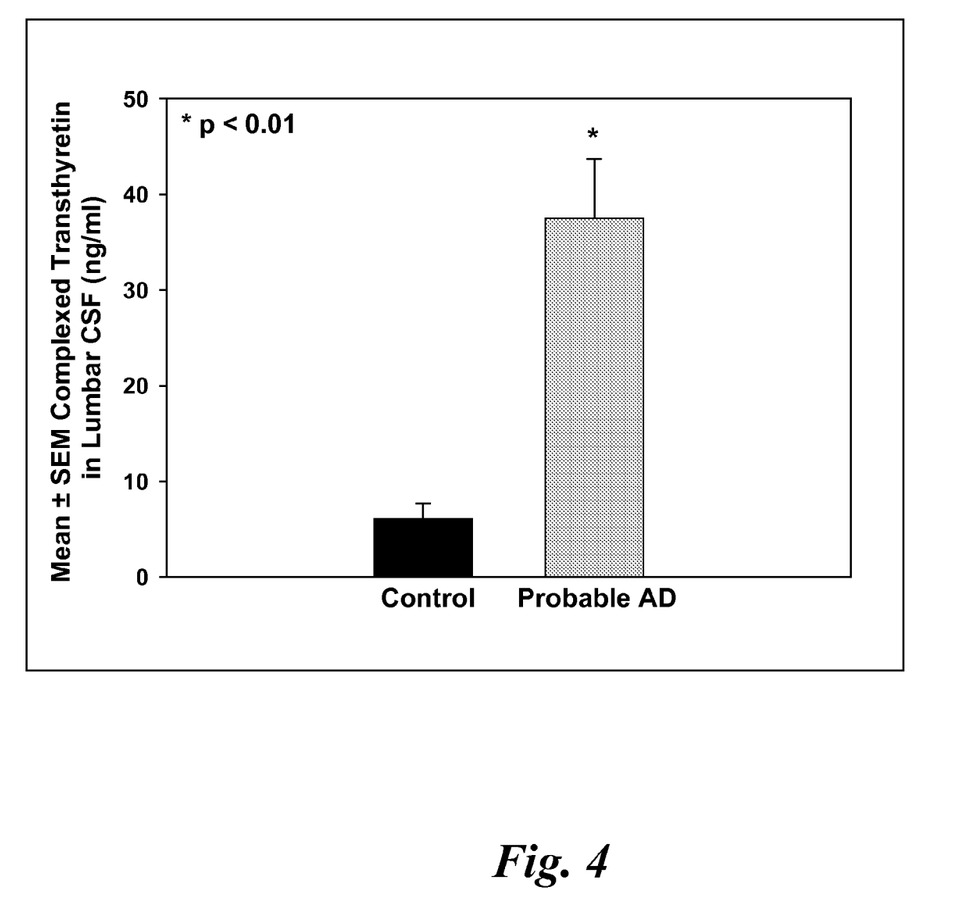
FIG. 4 is a graph showing mean±SEM levels of the biomarker protein complex measured as ng/ml complexed transthyretin in lumbar CSF from living probable AD and age-matched control subjects.

FIG. 4 shows a statistically significant 10 fold increase in levels of the protein complex measured as ng/ml transthyretin in probable AD subjects.

Figure 5:
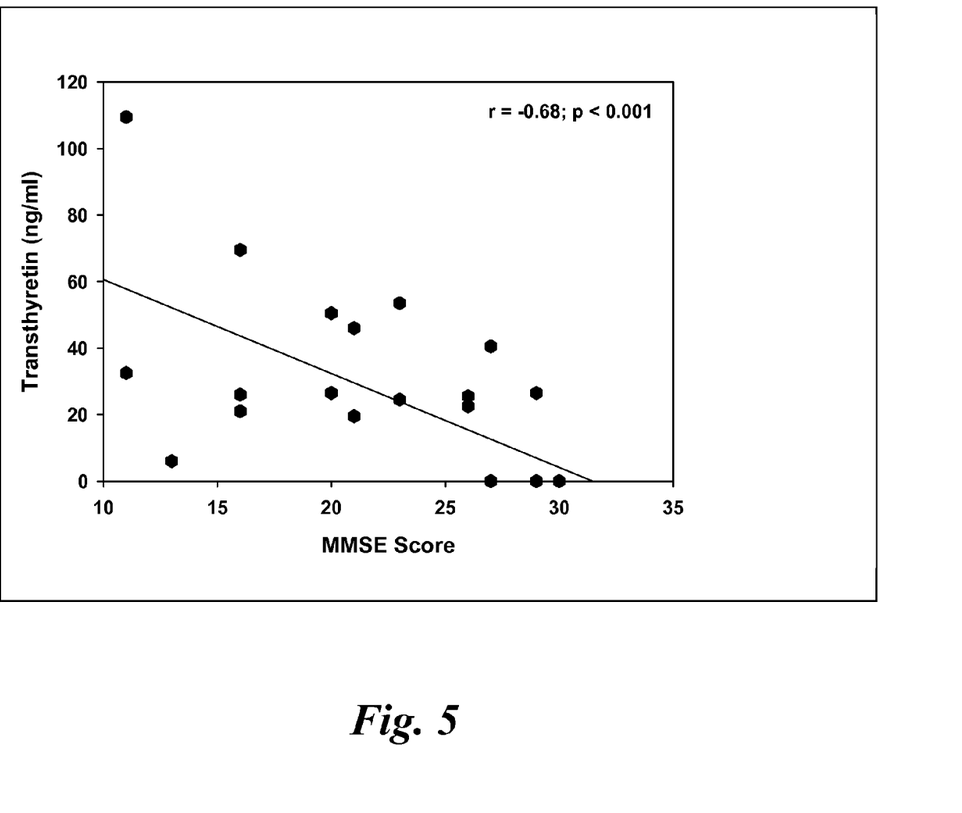
FIG. 5 is a graph showing levels of the protein complex significantly negatively correlate with mini mental status examination (MMSE) scores (lower MMSE—diminished cognitive function).

Additionally there is a statistically significant negative correlation between levels of the protein complex measured as ng/ml transthyretin and mini-mental status examination (MMSE) scores, a measure of cognitive function (FIG. 5).

Correlation analysis shows there is no statistically significant relationship between age and levels of the protein complex. Additionally, there are no sex related differences.

Use of Modified Forms of a Biomarker

It has been found that proteins and protein complexes frequently exist in a sample in a plurality of different forms characterized by differences in phosyphorylation, glycosylation and oxidative modification including aldehyde modification by compounds such as levuglandin, HNE and acrolein. Because the antibodies are able to recognize the protein regardless of posttranslational modifications the assay may be carried out as described. All the protein and protein complex modifications that would be understood by one of ordinary skill in the art are within the scope of the present invention.

Of course, embodiments of the present invention includes various nomenclature forms. For example, cystatin C is also known as neuroendocrine basic polypeptide, Gamma-trace, Post-gamma-globulin. Transthyretin is also known as prealbumin, TBPA, TTR, ATTR. Plasma retinol-binding protein is also known as PRBP, RBP. Phosphatidylethanolamine-binding protein is also known as PEBP, prostatic binding protein, HCNPpp, neuropolypeptide h3, Raf kinase inhibitor protein, RKIP. Carbonic anhydrase 2 is also known as EC 4.2.1.1, Carbonic anhydrase II, Carbonate dehydratase II, CA-II, Carbonic anhydrase C. Prostaglandin-H2 D-isomerase is also known as EC 5.3.99.2, Lipocalin-type prostaglandin-D synthase, Glutathione-independent PGD synthetase, prostaglandin-D2 synthase, PGD2 synthase, PGDS2, PGDS, Beta-trace protein, Cerebrin-28. Serotransferrin is also known as transferrin, siderophilin, beta-1-metal binding globulin.

Detection of Biomarkers for Alzheimer's Disease

The biomarkers of this invention can be detected by any suitable method including Western blot analysis and ELISA as described herein. ELISA is a preferred technique because of its ease of use.

Determination of Risk of Developing Disease

In one embodiment of the present invention is a method for determining the risk of progressing from amnestic MCI to AD in a subject. Biomarker amounts show significant positive correlations with Braak staging scores that measure the degree of neuropathology (specifically NFT) and significant negative correlations with MMSE (mini-mental status examination scores) that measure cognitive function. Based on the concentrations of the protein complex, MCI subjects with higher levels would be projected to advance to AD.

Data Analysis

Results of the assay will be compared statistically using analysis of variance to compare disease progression related differences. Post hoc testing will be carried out for pairwise comparisons (i.e., control vs. MCI).

Determining Course (Progression/Remission) of Disease

In one embodiment, this invention provides methods for determining the course of Alzheimer's disease in a subject. Disease course refers to changes in disease status over time, including disease progression (worsening) and disease regression (improvement). Over time, the amounts or relative amounts (e.g., the pattern) of the biomarkers changes. For example, the concentrations of biomarkers would be expected to decrease with appropriate pharmacologic interventions. The course of disease may be determined based on comparisons. Similarly, this method is useful for determining the response to treatment. If a treatment is effective, then the biomarkers will trend toward normal, while if treatment is ineffective, the biomarkers will trend toward disease indications.

An embodiment of the present invention is methods of identifying complexes that can be used as biomarkers of the present invention, the biomarkers being useful for diagnosis, aiding in diagnosis, stratifying, assessing risk, monitoring and/or predicting a neurological disease. Using methods described herein, protein spots representing different proteins can be identified as significantly different between LAD and control subjects. In one example, molecular weight (MW) fractionation of ventricular CSF specimens from 5 LAD and 5 age-matched controls can be separated into fractions greater than and less than about 50 kDa and subjected to 2-dimensional electrophoresis. Following a comparison of the gels, protein spots representing different proteins were identified as significantly different between LAD and control subjects. Examples of the proteins identified were beta-2-microglobulin, cystatin C, Cu/Zn superoxide dismutase, transthyretin, plasma retinol-binding protein, phosphatidylethanolamine-binding protein, carbonic anhydrase 2, prostaglandin-D-synthase, and serotransferrin. The present inventors found that the majority of the proteins identified in the greater than 50 kDa fraction normally weigh less than 50 kDa and should have been isolated in the lighter fraction. Based on this observation, the present inventors determined the presence of a complex. To confirm that the proteins are present as a complex, CSF samples from 8 LAD and 7 age-matched controls are subjected to MW fractionation, freeze dried, resuspended in 30 μl PBS and subjected to Western blot analysis and probed for PDS and TTR. Subject demographic data are shown in Table 1, below.

TABLE 1

Subject demographic data for ventricular CSF specimens.

|  | Mean ± SEM Age (y) | Sex | Mean ± SEM PMI (hr) | Median Braak Staging Score | Mean ± SEM complexed TTR Fold inc over control |
|---|---|---|---|---|---|
| Control | 83.3 ± 2.3 | 4M/3F | 3.4 ± 0.4 | I | 1.0 ± 0.4 |
| Non-AD Neurologic Disorders | 70.4 ± 4.2* | 7M/5F | 4.7 ± 1.6 | II | 1.4 ± 0.2 |
| MCI | 89.8 ± 1.4* | 2M/2F | 4.2 ± 1.8 | IV* | 2.9 ± 0.5* |
| EAD | 89.5 ± 2.7 | 1M/3F | 2.8 ± 0.7 | V* | 3.7 ± 0.3* |
| LAD | 81.6 ± 2.0 | 4M/4F | 3.1 ± 0.1 | VI* | 9.7 ± 2.2* |

*p < 0.05

There were no significant differences in age or post mortem interval (PMI) between LAD and control subjects. Median Braak staging scores were significantly higher in LAD (median=VI) compared to controls (median=I). A use of the monoclonal PDS antibody showed the presence of native PDS (MW=21 kDa) and a strongly immunopositive band at ~55 kDa that was more strongly stained in AD specimens than in controls. Stripping and reprobing the gels for TTR showed an immunopositive band corresponding to native TTR (MW=16 kDa) and the band at ~55 kDa. To verify specificity of the antibodies, representative LAD CSF specimens were subjected to Western blot analysis using antibodies that had been pretreated with representative immunizing proteins.

To determine if the protein complex is present at early stages of AD and is specific for AD, the present inventors carried out Western blot analyses of ventricular CSF samples from 4 subjects with MCI, 4 EAD subjects and 12 subjects with non-AD neurologic diseases including PD (N=2), PSP (N=2), DLB (N=5), and FTD (N=3). Table 1 shows subject demographic data. There were no significant differences in age between controls, LAD or EAD subjects. MCI subjects were significantly older than control subjects and subjects with non-AD pathologies were significantly younger than controls. Median Braak staging scores were significantly higher in MCI (median=IV), EAD (median=V) and LAD (median=VI) subjects compared with controls (median=I). There were no significant differences in post mortem intervals for any of the subjects. Measurement of staining intensity of the individual native proteins showed no significant differences between LAD and control subjects for TTR although PDS was significantly elevated in LAD CSF. However, there was considerable overlap of individual subjects from the two populations suggesting limited use of the native proteins as biomarkers. Staining intensity of the 55 kDa band was calculated as % of control staining for each gel for each of the antibodies. Because we hypothesized the amount of the complex, and not the native proteins, is indicative of AD, the present inventors calculated the product of the two percentages. Table 1 shows the mean±SEM product of the % control staining intensities for control, non-AD pathologies, MCI, EAD and LAD subjects and shows a significant disease progression related increase in the protein complex with statistically significant elevations of the complex in MCI, EAD and LAD subjects compared with control subjects. To be an effective biomarker of AD, the substance being studied in CSF must be present in brain. To determine if the protein complex is present in AD brain, preliminary studies were carried out to determine if the protein complex could be detected in representative specimens of HPG from LAD and control subjects. Specimens of HPG (N=4 LAD and 4 control) were homogenized in HEPES buffer and subjected to Western blot analysis.

Preliminary confocal analyses of sections of HPG immunostained for CNPase, a marker of oligodendrocytes or GFAP, a marker of glia concurrently with TTR and PDS show PDS is primarily associated with CNPase-positive oligodendrocytes whereas TTR is more strongly associated with GFAP-positive astrocytes. Comparison of LAD and control staining shows considerably higher levels of TTR and PDS in LAD brain compared to age-matched controls.

Based on the Western blot analyses, the present inventors initiated development of an enzyme linked immunoassay (ELISA) based on capture of one component of the complex and quantification of another component from small volumes of CSF. Using standard techniques for the optimization of ELISA conditions, a serial dilution matrix analysis was carried out using antibody concentrations between 0 and 1000 ng/ml PBS containing 0.05% sodium azide (PBSN). We tested both anti-TTR and anti-PDS as the trap antibody with the other as the probe antibody. Based on these studies an ELISA was established in which 96 well microtiter plates were coated overnight with mouse anti-PDS raised against recombinant human PDS at 1 µg/ml PBSN. The plates were rinsed and blocked for 1 hr using 5% dry milk/15% normal goat serum in PBSN and incubated with unprocessed CSF. Following 5 washes of PBSN, levels of TTR present in the trapped complex were quantified using rabbit anti-TTR raised against amino acids 1-147 of human TTR (1 µg/ml in blocking buffer) and horseradish peroxidase conjugated goat anti-rabbit secondary antibody (1:1000 dilution/blocking buffer). Color was developed using 3,3',5,5'-tetramethylbenzidine (TMB) color reagent followed by addition of stopping solution. Absorbance was read at 450 nm using a multi-well UV-Vis plate reader. Concentrations of TTR were quantified using a calibration curve of known concentrations of human TTR (0 to 500 ng/ml) coated in triplicate on each plate.

To determine limits of detection (LOD) and mean correlation coefficients using this approach, replicate analyses of standard solutions of TTR were carried out using 0, 25, 50, 100, 250 and 500 ng/ml TTR in PBSN (6 wells/plate; 3 plates). Calculation of correlation coefficients showed a statistically significant ($p<0.01$) positive correlation ($r=0.92\pm0.02$) between concentration and absorbance suggesting a good linearity of response over a wide concentration range. Calculation of mean LOD showed a mean±SEM value of $3.6\pm0.7$ ng/ml.

To verify the ELISA described above provides similar results to those observed using Western blot anlaysis, aliquots of unprocessed ventricular CSF from subjects were subjected to the ELISA in triplicate. Table 2, below shows results of the analyses for individual subjects and shows that there is no overlap of the subject populations.

TABLE 2

Individual complexed TTR concentrations (ng/ml CSF) in ventricular CSF.

| Control | Non-AD Pathologies | MCI | EAD | LAD |
|---|---|---|---|---|
| <5 ng/ml | <5 ng/ml | 93.0 | 175.0 | 205.0 |
| <5 ng/ml | <5 ng/ml | 110.0 | 139.5 | 61.0 |
| <5 ng/ml | <5 ng/ml | 93.0 | 93.0 | 27.5 |
| <5 ng/ml | <5 ng/ml | 192.0 | 74.0 | 46.5 |
| <5 ng/ml | <5 ng/ml | | | 74.0 |
| <5 ng/ml | <5 ng/ml | | | 141.0 |
| <5 ng/ml | <5 ng/ml | | | 262.5 |
| <5 ng/ml | <5 ng/ml | | | |
| | <5 ng/ml | | | |
| | <5 ng/ml | | | |
| | <5 ng/ml | | | |
| | <5 ng/ml | | | |
| <5 ng/ml | <5 ng/ml | 122 ± 23.7* | 120.0 ± 17.3* | 115.4 ± 19.6* |

*$p<0.05$

Control subjects and those with non-AD pathologic disorders showed levels below detection limits (<5 ng/ml) whereas all MCI, EAD and LAD subjects showed values considerably higher than the LOD. Comparison of mean values using Student's t-test showed concentrations of complexed TTR were significantly elevated in MCI, EAD and LAD CSF compared to control subjects (Table 2). As was observed for Western blot analyses, there were no differences between control and non-AD pathologies. Although these data represent a small number of subjects, it demonstrates 100% sensitivity and 100% specificity for the identification of subjects at all stages of AD including MCI. Because a suitable biomarker of AD should correlate with some aspect of the neuropathology, correlation analyses were carried out for all subjects comparing Braak staging score, a measure of NFT pathology, and levels of complexed TTR and showed a statistically significant ($p<0.01$) positive correlation ($r=+0.66$) between levels of complexed TTR and Braak score. Based on these data, use of a protein complex consisting of TTR and PDS appears to be efficient in the identification of AD subjects at all stages of AD including MCI in ventricular CSF specimens.

To be effective as a diagnostic biomarker for AD, the 55 kDa protein complex identified must be present at a quantifiable level in a relatively easily sampled fluid such as lumbar CSF. To determine if the protein complex is present in lumbar CSF, specimens were obtained from 15 living probable AD subjects and 14 age-matched control subjects and were analyzed in a doubly blinded fashion using the ELISA described above. Table 3, below, shows subject demographic data. There were no significant differences in age between AD and control subjects. Mean MMSE scores were significantly ($p<0.05$) lower in AD subjects (19.3±2.4) compared to controls (29.2±0.2).

TABLE 3

Subject demographic data for living probable AD and control subjects.

|  | Mean ± SEM Age (y) | Sex | Mean ± MMSE Score | Mean ± SEM TTR (ng/ml) |
| --- | --- | --- | --- | --- |
| Control | 71.0 ± 1.9 | 10 M/4 F | 29.2 ± 0.2 | 37.5 ± 6.2* |
| Probable AD | 68.4 ± 1.8 | 5 M/10 F | 19.3 ± 1.4* | 1.9 ± 1.9 |

*p < 0.05

Table 4 shows results of the analyses for individual subjects and shows that 13 of 14 control subjects had complexed TTR concentrations below the LOD whereas all 15 probable AD subjects had levels higher than the LOD. Mean complexed TTR concentrations in AD lumbar CSF (37.5±6.2 ng/ml) were ~⅓ those observed in ventricular CSF (110±5 ng/ml) but were significantly higher than the mean level in control subjects (6.1±1.6 ng/ml). The control mean±SEM was calculated using 5 ng/ml for LOD values.

TABLE 4

Individual complexed TTR concentrations for living probable AD and control subjects.

| Control | Probable AD |
| --- | --- |
| <5 ng/ml | 40.5 |
| <5 ng/ml | 32.5 |
| <5 ng/ml | 50.5 |
| <5 ng/ml | 46 |
| <5 ng/ml | 26 |
| <5 ng/ml | 69.5 |
| <5 ng/ml | 53.5 |
| <5 ng/ml | 24.5 |
| <5 ng/ml | 22.5 |
| <5 ng/ml | 21.0 |
| <5 ng/ml | 26.5 |
| <5 ng/ml | 109.5 |
| <5 ng/ml | 25.5 |
| 26.5 | 19.5 |
|  | 6.0 |
| Mean ± SEM = 6.1 ± 1.6 | Mean ± SEM = 37.5 ± 6.2 |

Calculation of sensitivity and specificity values for this relatively small sample size showed a sensitivity of 100% and a specificity of 93%. Correlation analysis of levels of complexed TTR and MMSE scores showed a statistically significant ($p<0.001$) negative correlation ($r=-0.68$) suggesting levels of the complex increase as cognitive function declines. Comparison of concentrations of complexed TTR as a function of gender showed no gender related differences.

The following non-limiting examples are presented as being exemplary of the present invention, and are not to be construed as limiting thereof.

EXAMPLE 1

Determining Presence of Biomarker in Sample

CSF samples were collected from 6 MCI, 4 EAD, 9 LAD and 8 age-matched control subjects at autopsy from the lateral ventricle using an 18 gauge cannula attached to virgin polypropylene syringes. Twenty to fifty milliliters of CSF were withdrawn, centrifuged at 10,000 g to pellet cells and aliquoted into 2 ml cryovials. The vials were immediately frozen in liquid nitrogen and maintained at −80° C. until used for analysis. For specificity studies CSF specimens were obtained in a similar manner from 5 subjects with diffuse Lewy body disease (LB), 2 subjects with Parkinson's disease (PD), 2 subjects with parasupranuclear palsy (PSP) and 3 subjects with frontotemporal dementia (FTD). Subjects used in these studies met standard histopathologic criteria for the diagnosis of AD (Mirra et al. Neurology 91:479-484 (1991); NIA-Reagan Institute Neurobiol Aging 18:S1-2 (1997). All control patients were followed longitudinally at the University of Kentucky Alzheimer's Disease Center (ADC) Clinic and had neuropsychological testing annually which remained in the normal range. All MCI patients were normal on enrollment into the University of Kentucky's longitudinal study and developed MCI during follow up. The criteria used for clinical diagnosis of amnesic MCI were those described by Petersen (Petersen et al. Arch Neurol 56:303-308 (1999) and include: 1) memory complaints corroborated by an informant, 2) objective memory impairment for age and education, 3) normal general cognitive function, 4) intact activities of daily living, and 5) the subject does not meet criteria for dementia. The clinical criteria for EAD were 1) a decline in cognitive function for a previous higher level, 2) declines in one or more areas of cognition in addition to memory, 3) a clinical dementia rating scale score of 0.5 to 1, and 4) a clinical examination that excluded other causes of dementia. All subjects had neuropathological evalution of sections of neocortex, hippocampus, entorhinal cortex, amygdala, basal ganglia, nucleus basalis of Meynert, midbrain, pons, medulla, and cerebellum using the modified Bielschowsky stain, hemotoxylin-eosin stain, and 10D-5 and alpha synuclein immunostains. Braak staging (Braak and Braak Acta Neuropathol 82:239-259 (1991) was determined using the Gallyas stain on sections of entorhinal cortex, hippocampus, and amygdala, and the Bielschowsky stain on the neocortex. None of the MCI, EAD, LAD, or control subjects demonstrated significant Lewy body pathology. The distinction between MCI and control patients was a significant increase in neuritic plaques in neocortical regions and a significant increase in neurofibrillary tangles in entorhinal cortex, hippocampus, and amygdala in MCI patients (Markesbery et al. Arch Neurol 63:38-46, 2006). Braak staging scores in control subjects were I to II and met the NIA-Reagan Institute low likelihood for the histopathological diagnosis of AD. The Braak staging scores of MCI subjects ranged from III to IV. EAD subjects met high likelihood criteria for the histopathogical diagnosis of AD with a Braak staging score of V. Braak staging scores in AD subjects were VI. Subjects with non-AD pathologies met standard histopathologic criteria for each disease.

Lumbar CSF samples were collected from subjects diagnosed with probable Alzheimer's disease (N=15) and subjects diagnosed as normal (non-demented) (N=14) the morning after fasting since midnight. The L3-4 or L4-5 interspace was infiltrated with 1% lidocaine using a 25 gauge needle for superficial and deep anesthesia. Lumbar puncture was performed with the patient in lateral decubitus or sitting using a 24 gauge Sprotte bullet tip atraumatic spinal needle and a 20 gauge spinal introducer. CSF was withdrawn using virgin 5 ml polypropylene syringes. Subjects were analyzed in a blinded fashion and were either probable AD subjects (N=15) or age-matched controls (N=14).

EXAMPLE 2

Measuring Levels of Biomarkers

Figure 6:
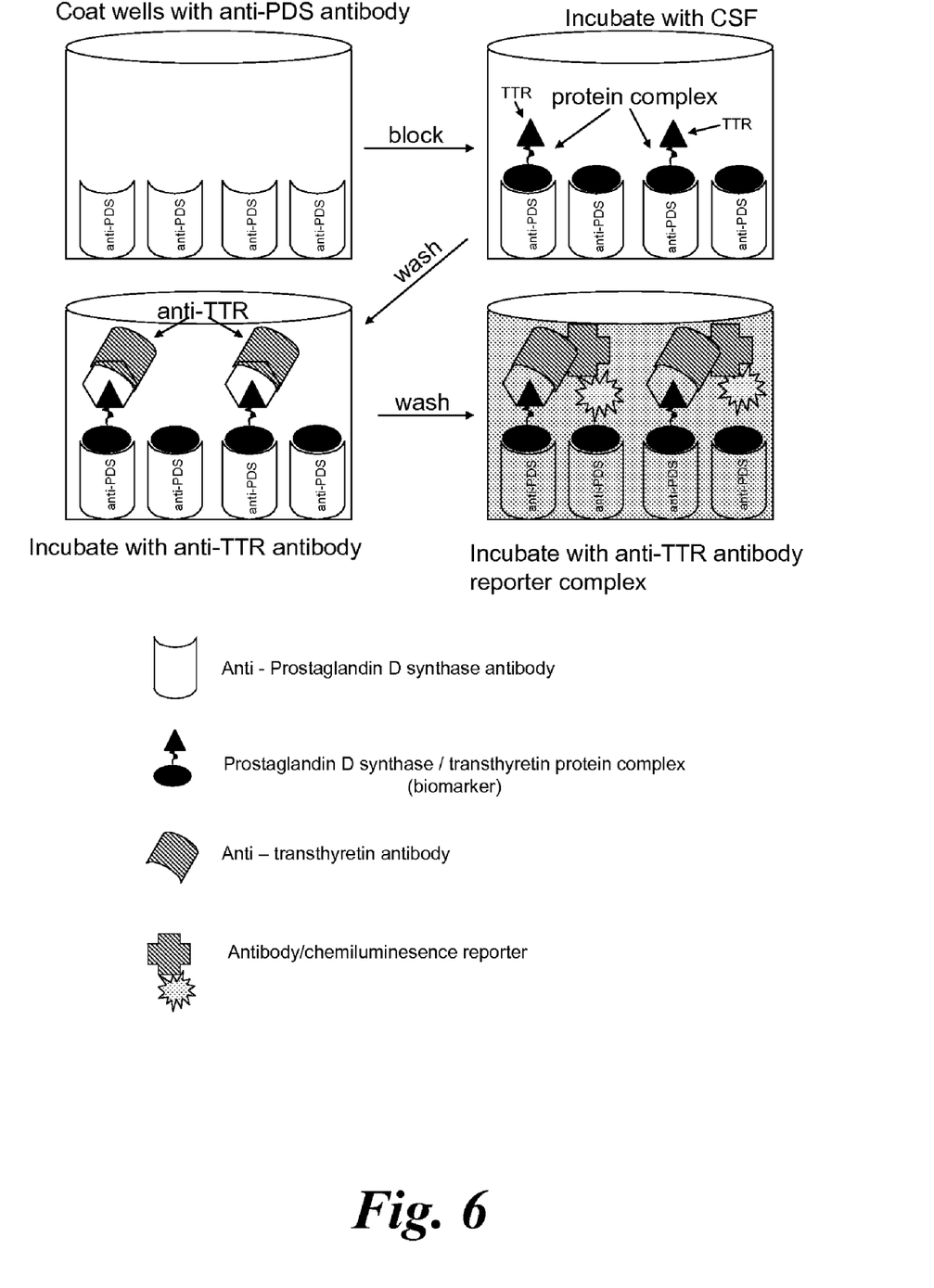
FIG. 6 is a diagram showing a sandwich ELISA protocol of the present invention.

To measure levels of the protein complex in CSF, a sandwich ELISA has been developed using standard protocols as described in *Techniques in Molecular Biology* and as shown schematically in FIG. 6. To trap the complex of interest, 96-well plates were coated overnight at 4° C. by adding 200 μl 1 μg/ml rat anti-human prostaglandin-D-synthase (Cayman Chemical, Ann Arbor, Mich. Catalog # 10004342) raised against recombinant human prostaglandin-D-synthase in PBS containing 0.1% $NaN_3$ (PBSN) per well. For quantification, one row of the plate is coated overnight with purified human transferin (Sigma Chemical, St. Louis, Mo.) at 25 ng/ml, 50 ng/ml, 125 ng/ml, 250 ng/ml, and 500 ng/ml in PBSN. After rinsing 5 times with PBSN (200 μl/wash), the plates are blocked for 2 hr with 100 μl 5% dry milk/15% goat serum in PBSN. The plates are washed 5 times with PBST and incubated 1 hr at room temperature with 50 μl untreated CSF. The plates are washed 5 times with PBST and are incubated 1 hr with 1 μg/ml rabbit anti-human transthyretin (Santa Cruz Biotechnology, Santa Cruz, Calif.; Catalog # sc-13098) prepared in 5% drymilk/PBSN. The transthyretin antibody is raised against amino acids 1-147 presenting full length human transthyretin. Following 5 washes in PBSN the plates are incubated with a 1:1000 dilution of horseradish peroxidase conjugated goat anti rabbit IgG (Jackson Immunoresearch, Laboratories, West Grove, Pa.; Catalog # 111035003) for 1 hr at room temperature. Following 5 washes in PBST, 100 μl 3,3',5,5'-tetramethylbenzidine (TMB) color reagent (Alpha Diagnostics, San Antonio, Tex.; Catalog # 80091) is added to each well for 30 minutes for color development. The reaction is stopped by addition of 50 μl stopping solution (Alpha Diagnostics, Catalog # 80100). The plates are read at 450 nm using a multi-well plate reader. Blanks for the assay consist of all reagents except CSF. Samples are analyzed in quadruplicate. To prevent edge effects the outer rows and columns of the plate are not used. Linear calibration curves are calculated for each plate and concentrations of CSF determined. Mean±SEM limits of detection of complexed transthyretin are 3.6±0.7 ng/ml. Mean±SEM correlation coefficients for replicate analyses of the calibration curve are 0.92±0.02 (p<0.01).

Complexed transthyretin concentrations (ng/ml CSF) are calculated based on the intensity of color developed from the horseradish peroxidase labeled secondary antibody and the TMB color reagent. The calibration curves constructed for each plate demonstrate linearity of response between color change as measured by absorbance at 450 nm and concentration of tranthyretin. The color development only occurs when the protein complex is present. For example, if uncomplexed prostaglandin-D-synthase is trapped during the initial phase of the measurement, it will not react with the subsequent antibody that recognizes only transthyretin. Antibody specificity was verified by preincubation of the antibodies with immunizing protein or peptide that blocked immunolabeling in Western blots.

Throughout this application, various publications are referenced. All such publications are hereby incorporated herein by reference in their entirety.

The invention thus being described, it would be obvious that the same may be varied in many ways. All such variances as considered to be embodiments of the present invention and not departures therefrom.

We claim:

1. A method for aiding diagnosis of mild cognitive impairment or Alzheimer's Disease in an individual, comprising:
    (a) obtaining a sample of cerebrospinal fluid from the individual;
    (b) measuring an amount of and/or a concentration of a protein biomarker complex that comprises transthyretin and prostaglandin-H2 isomerase in said sample; and
    (c) comparing the measured amount and/or concentration to a reference value, wherein a greater measured amount and/or concentration of the biomarker complex as compared to the reference value is indicative of a higher likelihood that the individual is afflicted with mild cognitive impairment or Alzheimer's disease, thereby aiding diagnosis of mild cognitive impairment or Alzheimer's disease in the individual.

2. The method of claim 1, wherein the reference value is based on a value from each of a plurality of samples, wherein the plurality of samples comprises at least one sample from each of a plurality of individuals afflicted with mild cognitive impairment or Alzheimer's disease.

3. The method of claim 1, wherein the reference value is based on a value from one or a plurality of samples obtained from the individual at one or a plurality of earlier points in time.

4. The method of claim 2, wherein the reference value is less than about 5 ng/mL.

5. The method of claim 2, wherein the reference value is about 5 ng/mL.

6. The method of claim 2, wherein the reference value is 5 ng/mL.

* * * * *